US008203336B2

(12) United States Patent
Peng et al.

(10) Patent No.: US 8,203,336 B2

(45) Date of Patent: Jun. 19, 2012

(54) EDDY CURRENT PROBES HAVING MAGNETIC GAP

(75) Inventors: Kang-Neng Peng, Longtan Shiang (TW); Ching-Shih Liu, Longtan Shiang (TW); Kang-Lin Hwang, Longtan Shiang (TW)

(73) Assignee: Atomic Energy Council Institute of Nuclear Energy Research, Taoyuan (TW)

( * ) Notice: Subject to any disclaimer, the term of this patent is extended or adjusted under 35 U.S.C. 154(b) by 291 days.

(21) Appl. No.: 12/558,531

(22) Filed: Sep. 13, 2009

(65) Prior Publication Data

US 2011/0062946 A1 Mar. 17, 2011

(51) Int. Cl.
*G01N 27/72* (2006.01)

(52) U.S. Cl. ......... 324/222; 324/240; 324/242; 324/228

(58) Field of Classification Search .................. 324/222, 324/242, 240, 228
See application file for complete search history.

(56) References Cited

U.S. PATENT DOCUMENTS

| | | | | |
|---|---|---|---|---|
| 3,694,740 | A * | 9/1972 | Bergstrand | 324/227 |
| 4,845,999 | A * | 7/1989 | Sobel | 73/862.335 |
| 5,926,020 | A * | 7/1999 | Samson | 324/238 |
| 6,670,808 | B2 * | 12/2003 | Nath et al. | 324/230 |
| 6,803,757 | B2 * | 10/2004 | Slates | 324/207.17 |
| 2005/0104703 | A1 * | 5/2005 | Watanabe et al. | 336/83 |
| 2007/0279050 | A1 * | 12/2007 | Edsinger et al. | 324/222 |
| 2009/0072822 | A1 * | 3/2009 | Sun et al. | 324/238 |

* cited by examiner

*Primary Examiner* — Arleen M Vazquez

(74) *Attorney, Agent, or Firm* — Jackson IPG PLLC; Demian K. Jackson

(57) ABSTRACT

An eddy current probe uses magnetic gap. The probe has a small size; and coil number in the probe is reduced. Hence, the probe can move easily inside and outside a tube and detect an end of the tube as close as possible.

6 Claims, 6 Drawing Sheets

11
12
13
2
111

EDDY CURRENT PROBES HAVING MAGNETIC GAP

FIELD OF THE INVENTION

The present invention relates to a probe; more particularly relates to providing a particular magnetic field lines loop to limit a magnetic field by a magnetic gap for obtaining high resolution and small size probe to move easily inside and outside a tubal object.

DESCRIPTION OF THE RELATED ARTS

In FIG. 4 and FIG. 5, general eddy current probes include absolute-type probes and differential-type probes. Coils wind around an air-cored probe and the probe is put on an outside or inside surface of a tubal object. Yet some physical characteristics, like edge effect, are limited in some cases. For example, a nuclear fuel rod may be especially damaged at two ends of the rod.

Moreover, the air-cored probe has many circle coils and thus internal resistance of the coils 3 is high, where an equivalent circuit of the probe is shown in FIG. 6. Its magnetic field affects a big area; distances between coils are widened to avoid mutual induction, and thus probe size is hard to be reduced in size. Since the probe is not reduced in size, detection for the tubal object is limited. In addition owing to the mutual induction between the coils on moving the probe along the tubal object, signals of measurement may not be exactly received and discriminability is thus lowered. Hence, the prior art does not fulfill all users' requests on actual use.

SUMMARY OF THE INVENTION

The main purpose of the present invention is to provide a probe to detect the defects near end of a tubal object with high discriminability.

The second purpose of the present invention is to provide the probe having a magnetic gap for high resolution detection.

The third purpose of the present invention is to provide the probe for detecting an end of the tubal object as close as possible with eddy current induction.

The fourth purpose of the present invention is to provide the probe with reduced mutual induction between coils to obtain high discriminability. With reduced probe size owing to shorten distances between coils, while the probe is able to move easily inside and outside the tubal object.

The fifth purpose of the present invention is to provide the probe for detection having a high Q value with reduced coil number around a high flux magnetic core and reduced coil internal resistance.

To achieve the above purposes, the present invention is an eddy current probe having a magnetic gap, comprising a high flux magnetic core, an excitatory coil, a support part and a detection part, where the high flux magnetic core surrounds an tubal object; the high flux magnetic core has an annular gap at a face of the high flux magnetic core facing the tubal object; the excitatory oil winds around the high flux magnetic core; the excitatory coil generates an eddy current in the tubal object by a part of the excitatory coil; the part of the excitatory coil is revealed toward the annular gap facing the tubal object; the support part supports and fixes the excitatory coil; the detection part excites the excitatory coil to generate a high-frequency magnetic field; the detection part obtains signals of the excitatory coil to analyze impedance changes of the excitatory coil. Accordingly, a novel eddy current probe having a magnetic gap is obtained.

BRIEF DESCRIPTION OF THE DRAWINGS

The present invention will be better understood from the following detailed descriptions of the preferred embodiments according to the present invention, taken in conjunction with the accompanying drawings, in which.

DESCRIPTION OF THE PREFERRED EMBODIMENT

The following descriptions of the preferred embodiments are provided to understand the features and the structures of the present invention.

Figure 1:
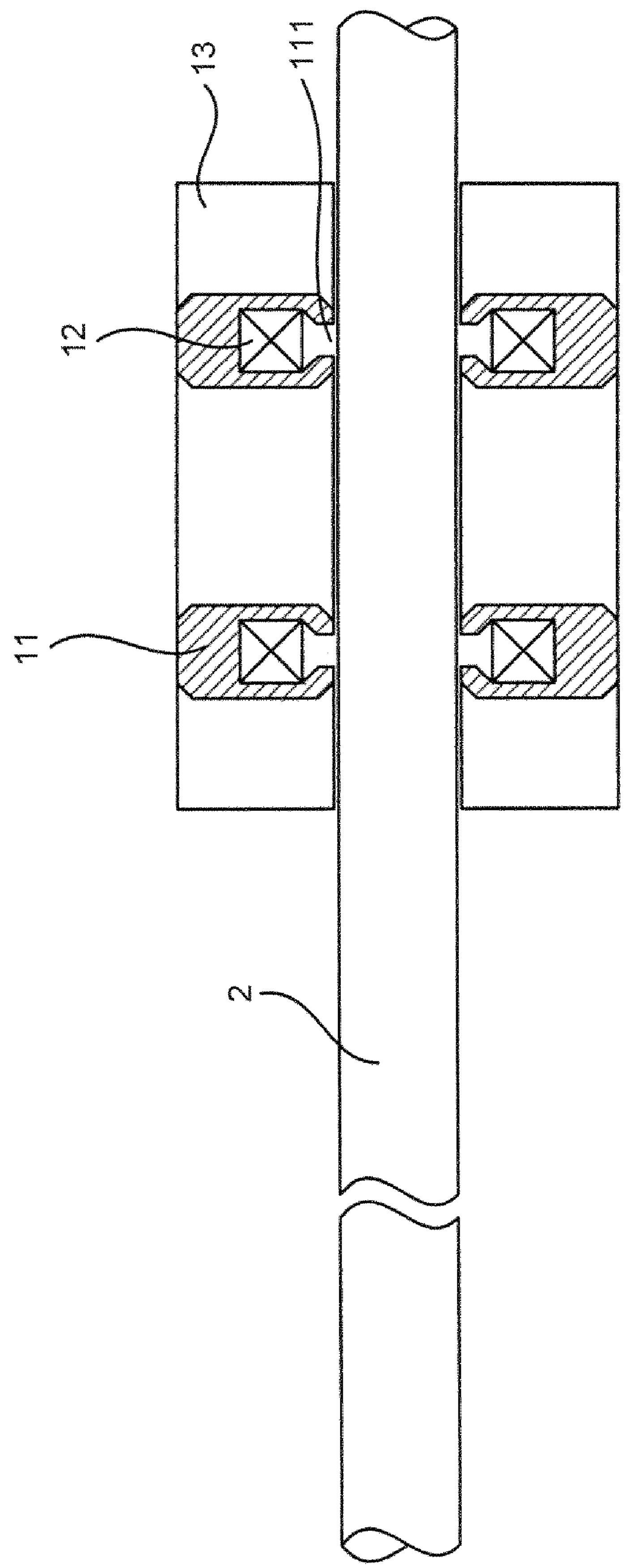
FIG. 1 is the view showing the first preferred embodiment according to the present invention.
Figure 2:
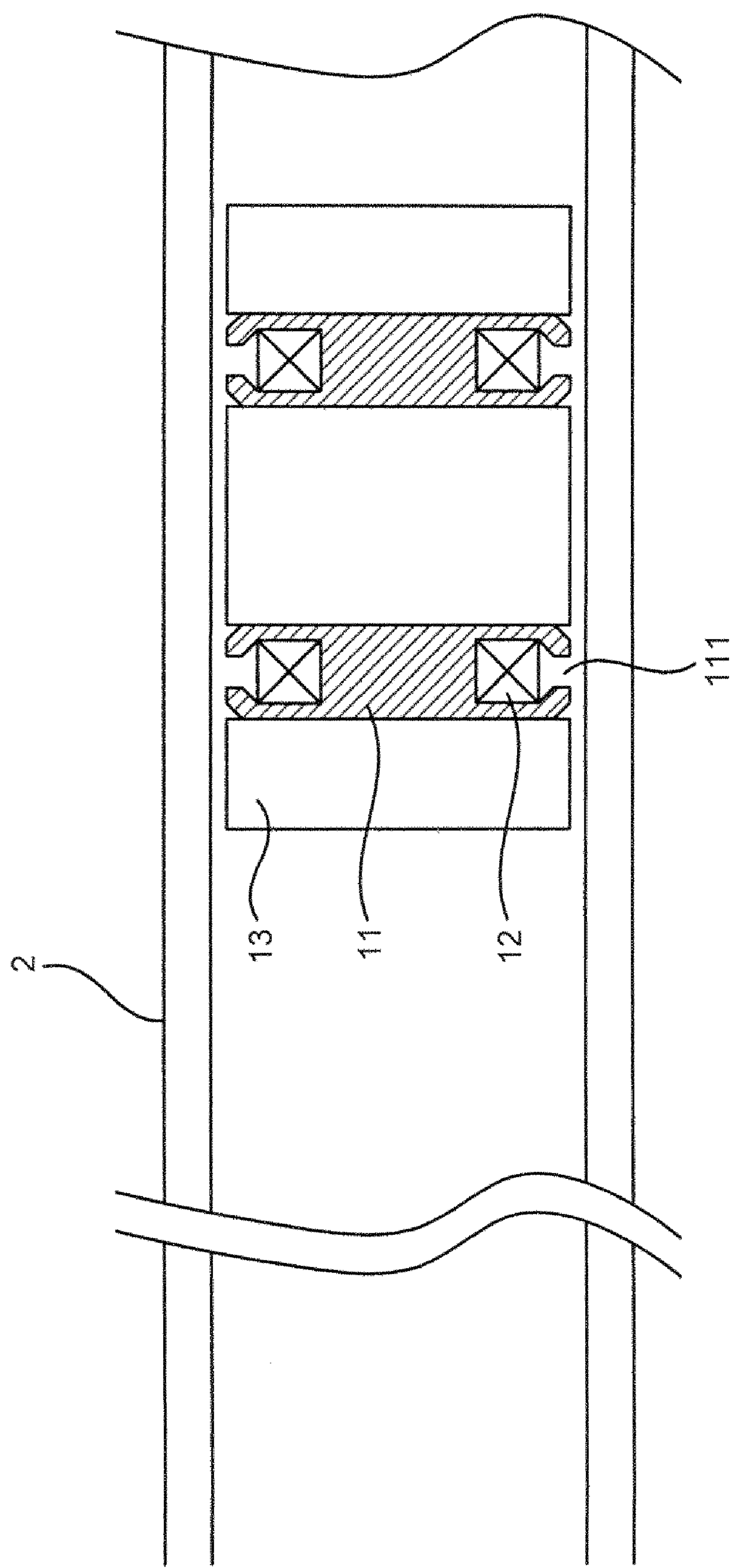
FIG. 2 is the view showing the second preferred embodiment according to the present invention.
Figure 3:
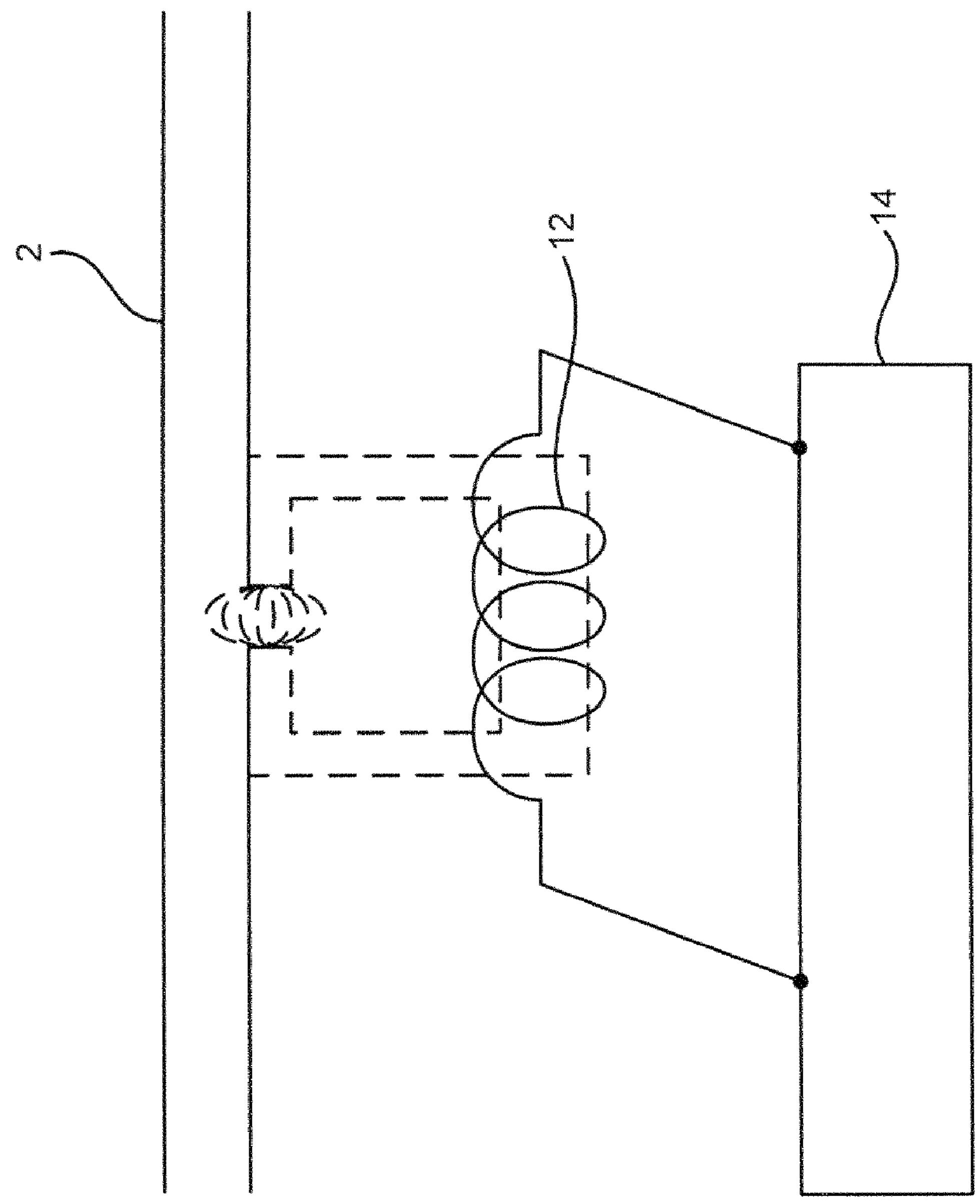
FIG. 3 is the view showing the equivalent circuit.
Figure 4:
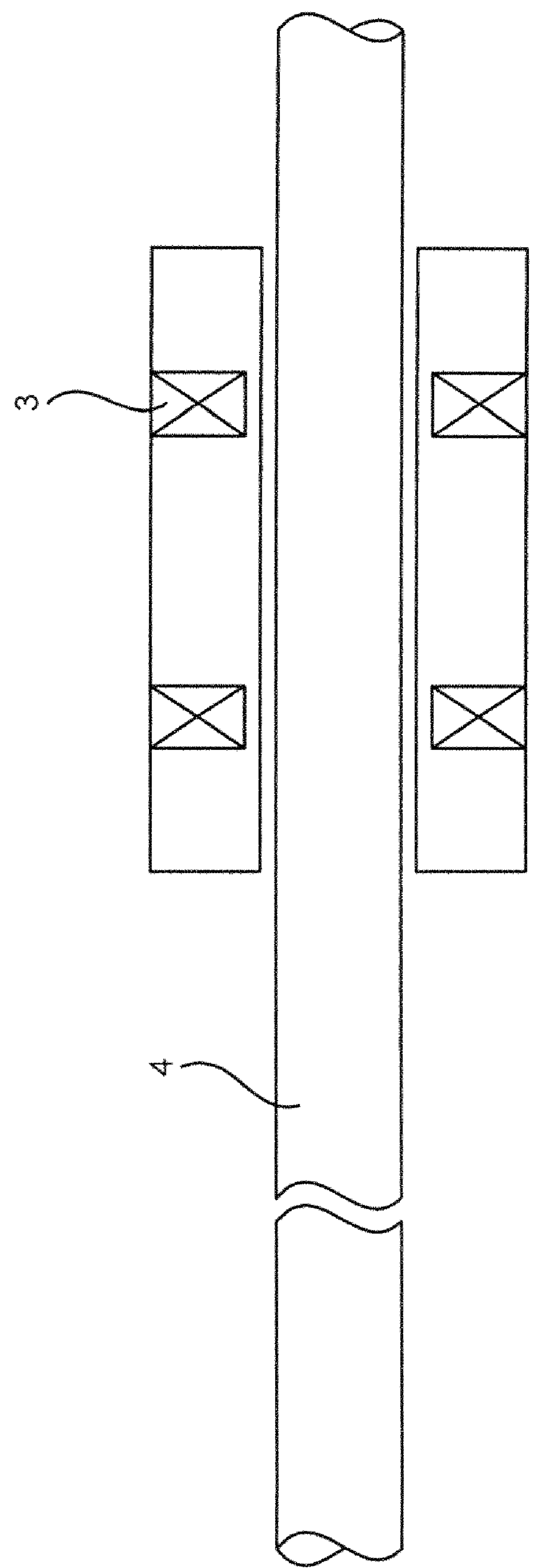
FIG. 4 is the view of outside detecting by the prior art.
Figure 5:
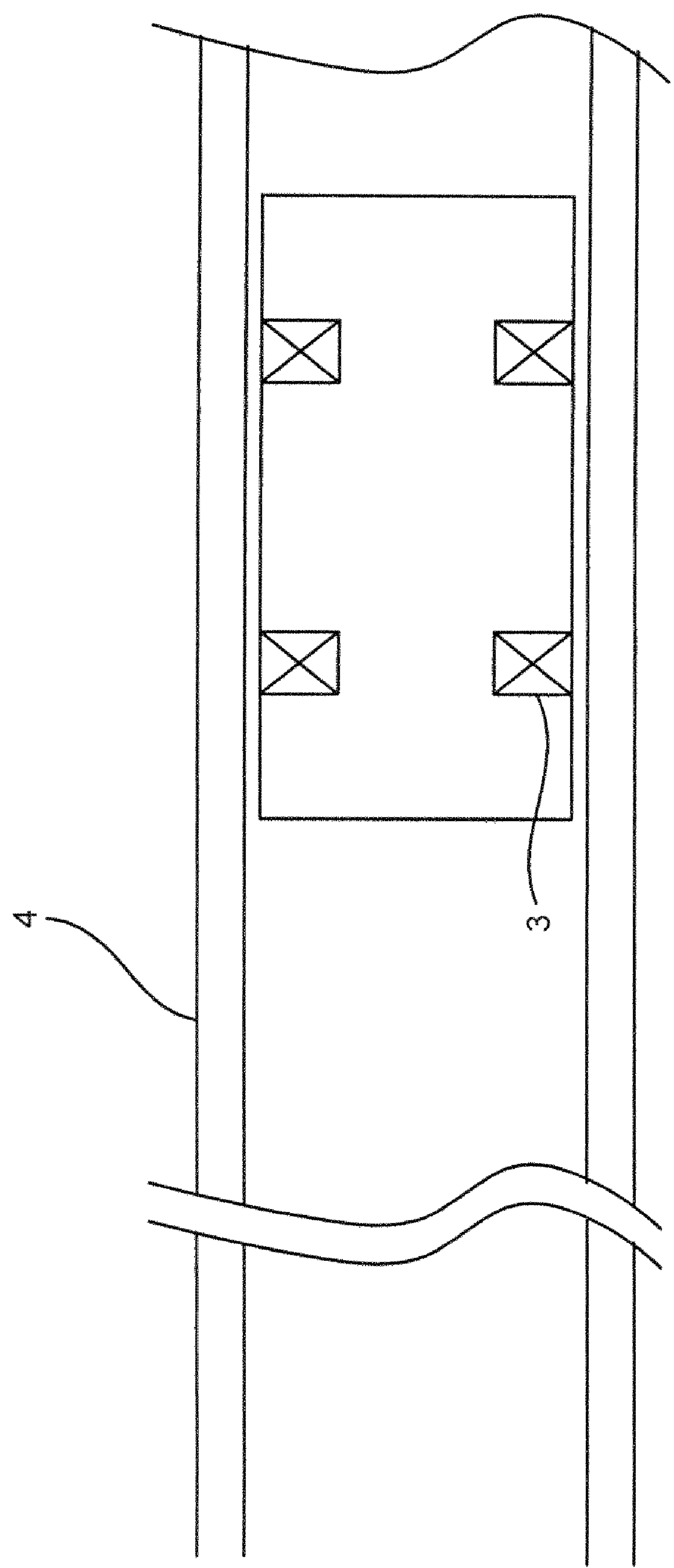
FIG. 5 is the view of inside detecting by the prior art.
Figure 6:
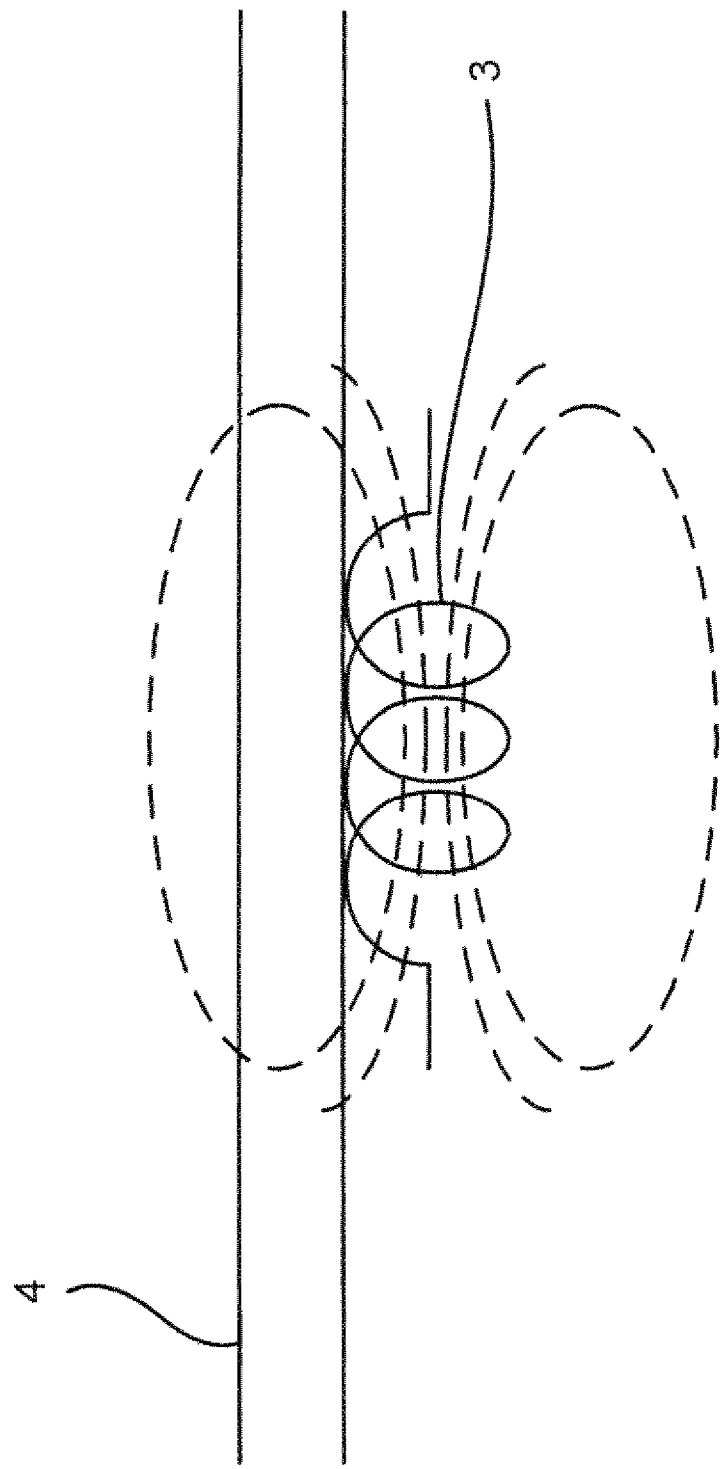
FIG. 6 is the view of the equivalent circuit of the prior art.

Please refer to FIG. 1 to FIG. 3, which are views showing a first and a second preferred embodiments according to the present invention; and a view showing an equivalent circuit. As shown in the figures, the present invention is an eddy current probe having a magnetic gap, comprising a high flux magnetic core 11, an excitatory coil 12, a support part 13 and a detection part 14, where a tubal object 2 is detected at an outside surface, an inside surface or an end of the tubal object 2.

The high flux magnetic core 11 has a U-shape and surrounds the tubal object 2, where the high flux magnetic core 11 has an annular gap 111 at a face facing the tubal object 2.

The excitatory coil 12 winds around the high flux magnetic core 11; and generates an eddy current in the tubal object 2 by a part of the excitatory coil 12 revealed toward the annular gap 111 facing the tubal object 2.

The support part 13 supports and fixes the excitatory coil 11.

The detection part 14 excites the excitatory coil 12 to generate a high-frequency magnetic field; and then obtains signals of the excitatory coil 12 to analyze impedance changes of the excitatory coil 12. Thus, a novel eddy current probe having a magnetic gap is obtained.

On using the present invention, the tubal object 2 of a nuclear fuel rod is obtained to be detected at an outside surface (in FIG. 1) and at an inside surface (in FIG. 2), where the high flux magnetic core 11 has the annular gap 111 smaller than 800 micrometers (μm). When the excitatory coil 12 is excited by a high-frequency current outputted from the detection part 14, each coil affects the tubal object 2 to obtain corresponding impedance. Impedance changes of the excitatory coil 12 are detected to find whether there are any defects of perforation, crevices or transmutation.

Thus, a particular magnetic field lines loop is provided to limit a magnetic field by the annular gap with the excitatory coil winding around the high flux magnetic core. The present invention has advantages of:

(a) high resolution, whose magnetic gap is very small scaled down to micrometers;

(b) small affected area, whose eddy current induction can be converged toward an end of a tubal object as close as possible;

(c) reduced mutual induction, whose mutual induction between coils is reduced to obtain high discriminability with probe size reduced as well owing to shorten distance between coils and the probe is thus able to move easily inside and outside the tubal object; and (d) high Q value whose number of coils and further internal resistance of the coils are reduced by using the high flux magnetic core.

To sum up, the present invention is an eddy current probe having a magnetic gap, where a particular magnetic field lines loop is provided with a magnetic gap to limit a magnetic field; and mutual induction between coils is reduced to obtain high discriminability with probe size reduced as well owing to shorten distance between coils and the probe is thus able to move easily inside and outside a tubal object.

The preferred embodiments herein disclosed are not intended to unnecessarily limit the scope of the invention. Therefore, simple modifications or variations belonging to the equivalent of the scope of the claims and the instructions disclosed herein for a patent are all within the scope of the present invention.

What is claimed is:

1. An eddy current probe having a magnetic gap, comprising:

a high flux magnetic core, said high flux magnetic core having an annular gap at a face of said high flux magnetic core configured to face a tubal object wherein said annular gap is smaller than 800 micrometers (μm);

an excitatory coil, said excitatory coil winding around said high flux magnetic core, said excitatory coil generating an eddy current in said tubal object by a part of said excitatory coil, said part of said excitatory coil being revealed toward said annular gap facing said tubal object;

a support part, said support part supporting and fixing said excitatory coil; and a detection part, said detection part exciting said excitatory coil to generate a high-frequency magnetic field, said detection part obtaining signals of said excitatory coil to analyze impedance changes of said excitatory coil, wherein a particular magnetic field lines loop is obtained to limit a magnetic field by said annular gap to detect said tubal object for defects of perforation, crevices, or transmutation.

2. The eddy current probe according to claim 1, wherein said high flux magnetic core and support part are configured to detect from a position of an outside surface, an inside surface and an end of said tubal object.

3. The eddy current probe according to claim 1, wherein said high flux magnetic core is made of a soft magnetic metal material.

4. The eddy current probe according to claim 3, wherein said soft magnetic metal material is ferrite.

5. The eddy current probe according to claim 1, wherein said tubal object is a nuclear fuel rod.

6. The eddy current probe of claim 1, wherein the high flux magnetic core has a U-shaped cross-section.

* * * * *